(12) United States Patent
Alexandre et al.

(10) Patent No.: US 7,559,920 B2
(45) Date of Patent: Jul. 14, 2009

(54) DEVICE FOR CONNECTING AN ACTIVE SUBSTANCE CONTAINER TO AN INJECTION NOZZLE IN A DEVICE USED TO INJECT SAID ACTIVE SUBSTANCE

(75) Inventors: Patrick Alexandre, Gray (FR); Georges Baud, La Crau (FR); Bernard Brouquieres, Toulon (FR)

(73) Assignee: Crossject, Paris (FR)

( * ) Notice: Subject to any disclaimer, the term of this patent is extended or adjusted under 35 U.S.C. 154(b) by 16 days.

(21) Appl. No.: 10/553,418

(22) PCT Filed: Apr. 15, 2004

(86) PCT No.: PCT/FR2004/000923

§ 371 (c)(1),
(2), (4) Date: Oct. 17, 2005

(87) PCT Pub. No.: WO2004/093947

PCT Pub. Date: Nov. 4, 2004

(65) Prior Publication Data

US 2006/0189927 A1    Aug. 24, 2006

(30) Foreign Application Priority Data

Apr. 16, 2003 (FR) .................................. 03 04762

(51) Int. Cl.
*A61M 5/00* (2006.01)
*A61M 5/30* (2006.01)

(52) U.S. Cl. ........................................ 604/240; 604/68

(58) Field of Classification Search ................. 604/110, 604/247, 240–243, 236, 238, 68–72
See application file for complete search history.

(56) References Cited

U.S. PATENT DOCUMENTS

| 4,150,672 | A | * | 4/1979 | Whitney et al. | ............. 604/155 |
| 4,479,801 | A | | 10/1984 | Cohen | |
| 5,919,159 | A | | 7/1999 | Lilley et al. | |
| 5,989,226 | A | | 11/1999 | Hymanson | |
| 6,017,330 | A | * | 1/2000 | Hitchins et al. | ............. 604/218 |
| 6,132,395 | A | | 10/2000 | Landau et al. | |
| 2001/0047153 | A1 | * | 11/2001 | Trocki et al. | ................ 604/155 |

FOREIGN PATENT DOCUMENTS

| WO | WO 01/30419 A2 | 5/2001 |
| WO | WO 02/34317 A1 | 5/2002 |

* cited by examiner

*Primary Examiner*—Kevin C Sirmons
*Assistant Examiner*—Elizabeth R MacNeill
(74) *Attorney, Agent, or Firm*—Oliff & Berridge, PLC

(57) ABSTRACT

The invention relates to an injection device which may or may not be equipped with a needle, comprising an injection nozzle and a tube which is intended to receive the active substance to be injected, whereby the tube is fixed to the nozzle using connecting means. The inventive device is characterized in that the aforementioned connecting means comprise at least three identical bosses which are solidly connected to the nozzle. Moreover, each of said bosses comprises an inclined part which terminates in a flange, said flange co-operating with a collar which is formed on the tube and acts as a backstop for the tube when the latter is connected to the nozzle.

14 Claims, 5 Drawing Sheets

COUPE A-A

FIG.5
COUPE A-A
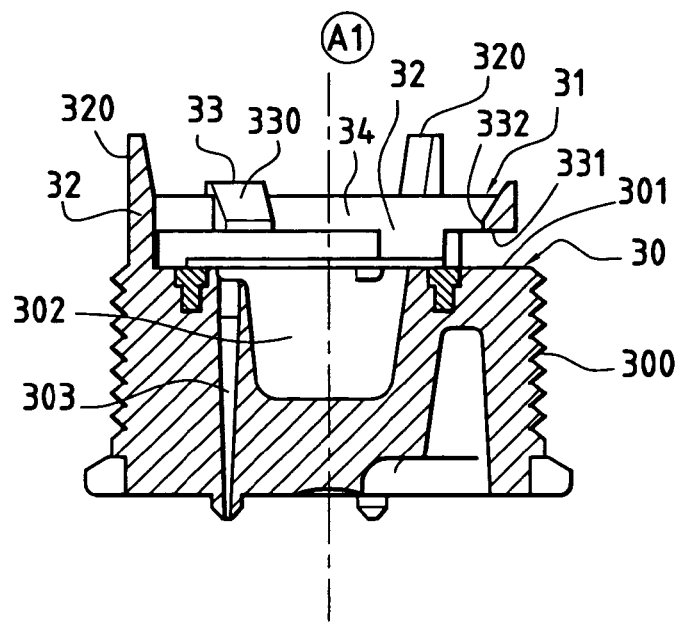
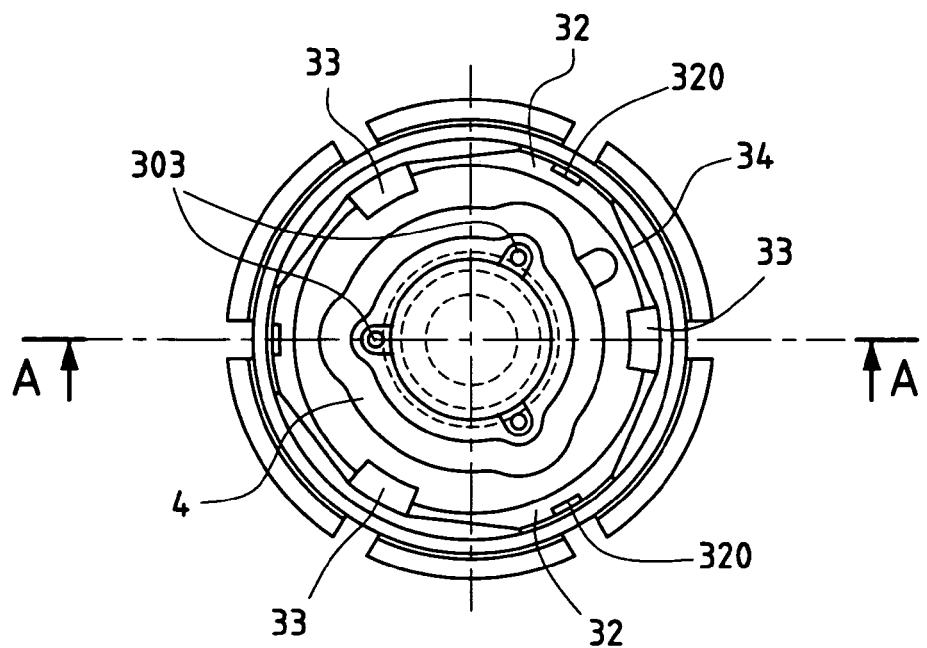
FIG.4

DEVICE FOR CONNECTING AN ACTIVE SUBSTANCE CONTAINER TO AN INJECTION NOZZLE IN A DEVICE USED TO INJECT SAID ACTIVE SUBSTANCE

The technical field of the invention is that of prefilled and disposable injection devices which may or may not be equipped with a needle and which function with an energy source, for example a gas generator, and are used for intradermal, subcutaneous and intramuscular injections of liquid active substance for therapeutic use in human or veterinary medicine.

The active substance is composed of a liquid of greater or lesser viscosity, a mixture of liquids, or a gel. The active substance can also be a solid dissolved in a suitable solvent for injection or can be a powdered solid in suspension at a certain concentration in a suitable liquid. The particle size of the active substance must then be compatible with the diameter of the conduits so as to avoid blocking them.

An injection device comprises in a known manner, for example as in patent application FR 2 815 544 (equivalent of WO 02/34317), a mechanical assembly and a pharmaceutical assembly. The mechanical assembly is composed in particular of a mechanism for actuating the device and of an energy source, formed for example by a pyrotechnic gas generator and intended for injecting the active substance through the patient's skin. The pharmaceutical assembly comprises the liquid active substance. The active substance is generally placed in a tube which is then intended to be inserted into the mechanical assembly. The two assemblies are generally assembled separately, the filling of the tube with the active substance having to be precisely controlled and carried out in an enclosed environment in order to avoid impurities infiltrating into the tube and contaminating the active substance. It is especially necessary that no impurities settle in the zones through which the active substance is to flow. To avoid infiltration of these impurities into the tube, the tube can be fitted, during production of the pharmaceutical assembly, on the nozzle for injecting the active substance and it can be pressed against said nozzle to create a leaktight connection between the two elements. The two elements, that is to say the tube filled with active substance and the injection nozzle constitute the pharmaceutical assembly. After the two elements of the pharmaceutical assembly have been joined together and the tube has been filled with the active substance, and before the pharmaceutical assembly is fitted on the mechanical assembly, a certain length of time may elapse during which the pharmaceutical assembly is transported and stored in an unenclosed environment, for example a warehouse. During this period, it is therefore necessary to maintain a perfect connection between the injection nozzle and the tube and good pressing of the tube against the injection nozzle in order to avoid penetration of impurities into the tube. In order to maintain a perfect connection between the nozzle and the tube, the nozzle must not be subjected to too much mechanical stress when fixing it on the tube.

U.S. Pat. No. 6,132,395 discloses a needleless injection device comprising a container and a nozzle made of polycarbonate intended to be fixed on the container formed by a glass tube. The nozzle is situated at one end of the tube and more particularly comprises four tabs which extend the entire length of the tube and end in bosses which allow the nozzle to be clipped onto the tube. The tabs thus form a claw which encloses the tube in order to fix the nozzle. In said patent, the nozzle is fixed directly by virtue of its tabs. The tabs bend outward along the entire length of the tube until the tube is completely enclosed. When the nozzle is being clipped onto the tube, this unique mechanical stressing of the tabs may create irreversible deformation of the tabs if they are made of a hard material such as polycarbonate, for example, and may thus lead to a poor connection between the tube and the nozzle.

The object of the invention is therefore to maintain a perfectly leaktight connection between the tube and the injection nozzle in order to avoid penetration of impurities into the tube when the pharmaceutical assembly is not yet fitted on the mechanical assembly to produce the complete needleless injection device.

This object is achieved by a device for injecting an active substance through a patient's skin, comprising in particular an injection nozzle and a glass tube intended to receive said active substance to be injected, said tube being fixed to said nozzle with the aid of connecting means, the connecting means comprising at least three identical bosses which are integral with the nozzle, said bosses each comprising an inclined part which is terminated by a flange, said flange cooperating with a collar which is formed on the tube and is situated at one of the ends of the tube, said collar serving as an anti-return element for the tube when the latter is connected to the nozzle, said device being characterized in that the bosses are connected to one another by connecting branches.

According to one particular feature, the connecting branches have a height of 1.4 mm. According to the invention, the thickness and height of the connecting branches are chosen so as to make the connecting branches sufficiently flexible to lengthen and bend in the area of the bosses during clipping-on of the tube. In particular, the flexibility of the connecting branches allows each of the bosses to match the shape of the glass tube.

According to another particular feature, the bosses are supported by the connecting branches, said connecting branches being made integral with the nozzle by means of connecting blocks and being connected to one another so as to define a substantially circular crown whose diameter is substantially equal to the external diameter of the collar of the tube. According to the invention, the geometry of the crown used for clipping the tube onto the nozzle has been designed to better distribute the stresses exerted on the tube.

Thus, by virtue of the presence of the connecting branches supporting the bosses, the deformation necessary for clipping the tube onto the nozzle is not limited to simple bending in the area of the bosses, but instead simultaneously consists of a lengthening of the connecting branches and a bending of these connecting branches in the area of each of the bosses. The connecting blocks ensure the rigidity and blocking of the clip connection between the tube and the nozzle.

According to the invention, each of the bosses constitutes a point of contact between the nozzle and the tube.

According to one particular feature, the inclined part of the bosses is inclined in the direction of the nozzle and toward the inside of the nozzle. This inclined part makes it possible, particularly when the tube is being clipped onto the nozzle, to guide the tube and gradually spread apart the bosses in order to allow the collar of the tube to pass these. The degree of inclination of this inclined part must be designed to limit as far as possible the force needed for spreading the bosses apart as the collar of the tube passes them.

According to another particular feature, each boss is inwardly curved, the bosses all being inscribed in a same circle whose diameter is substantially equal to the external diameter of the collar of the tube. According to the invention, the force with which the tube is pressed against the nozzle is therefore not distributed, in the area of each boss, on one contact point, but instead on a line or even on a surface.

According to another particular feature, the angle of opening defined by the two segments joining the center of the circle to the ends of each inwardly curved boss is between 17 and 23 degrees. According to the invention, for each boss the greater the angle defined above, the better will be the distribution of the stresses on the glass tube.

According to another particular feature, the bosses are spaced apart from one another at regular intervals. The spacing of the bosses has to be uniform in order to obtain a homogeneous distribution of the stresses on the tube.

According to another particular feature, the nozzle has a flat surface, the bosses being situated at a non-zero distance from said surface, the space between the flange of the bosses and said surface substantially corresponding to the thickness of the collar of the tube.

According to another particular feature, the end of each of the bosses has a rounded shape. The line of contact of each of the bosses with the tube is situated at the summit of the rounded part. The rounded part thus makes it possible to eliminate any sharp edge and thus limit any damage to the glass tube.

According to another particular feature, the diameter of the circle within which the bosses are inscribed is 13.2 mm, and the rounded shape of the bosses has a radius of 0.1 mm. According to the invention, the greater the diameter of the circle, the more stable is the connection of the tube to the nozzle and the weaker the forces exerted on the glass tube.

According to one embodiment, each boss is supported by a rod which is fixed to the nozzle and is able to deform elastically.

According to a preferred embodiment of the invention, the nozzle, the bosses, the connecting branches and the connecting blocks are made as one piece.

According to one particular feature, the piece formed by the nozzle, the bosses, the connecting branches and the connecting blocks is made from polycarbonate. According to the invention, the material constituting this piece must be able to satisfy a number of conditions. In particular, this material will have to be sufficiently hard to be traversed by the liquid active substance without deteriorating, and it will have to be sufficiently flexible to be able to be clipped onto the tube. Moreover, this material will have to be approved for use in the field of pharmacy and must not be aggressive with respect to glass so as not to scratch and damage the tube.

According to a preferred embodiment of the invention, the injection device is needleless and comprises, as energy source for injection of the active substance, a pyrotechnic gas generator.

The invention, with its characteristics and advantages, will become clearer from reading the description given with reference to the attached drawings, in which:

FIG. 4 depicts, in plan view, the injection nozzle shown in FIG. 2.

FIG. 5 depicts a longitudinal section, along line A-A, of the injection nozzle shown in FIG. 4.

Figure 1:
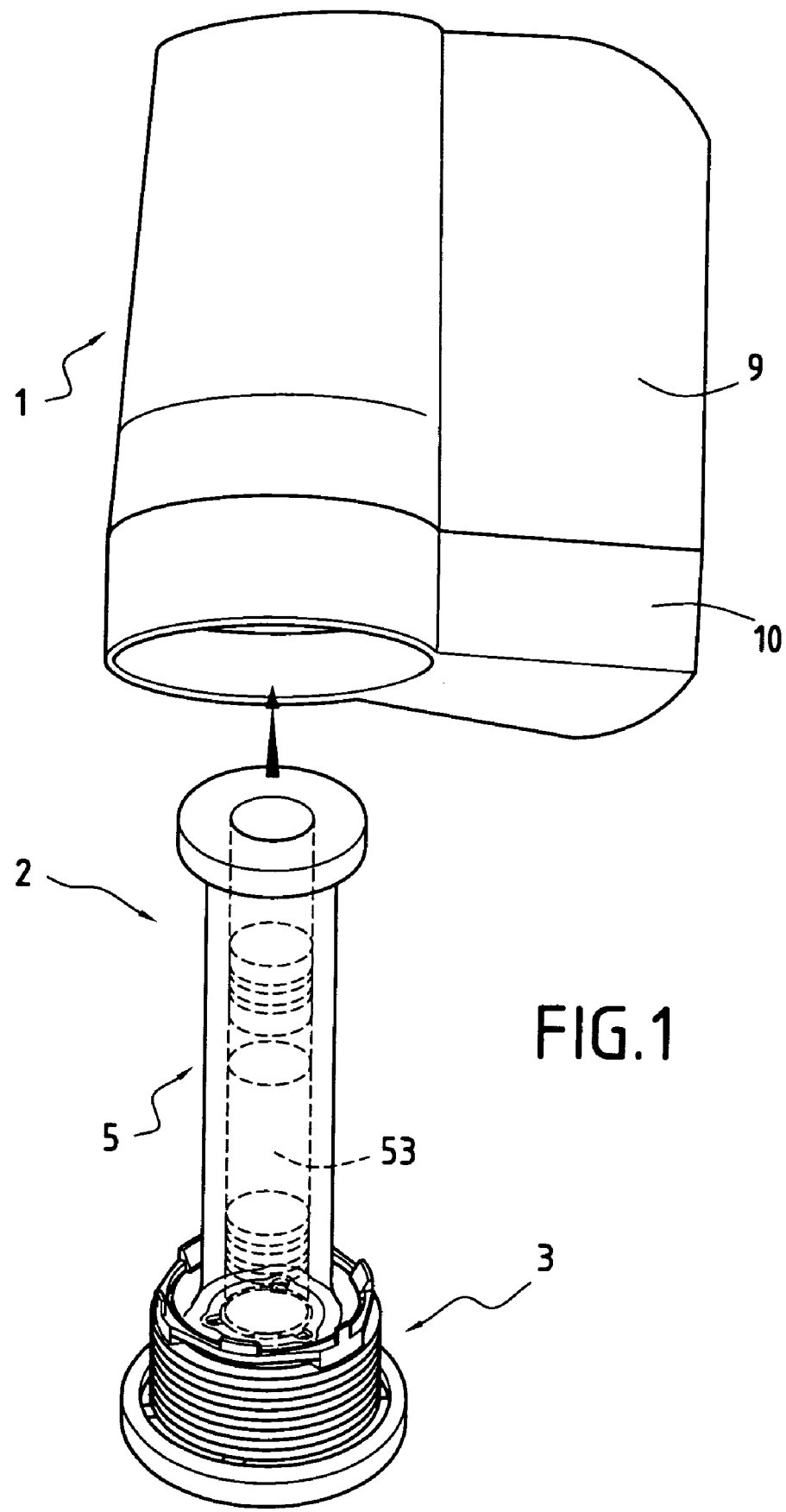
FIG. 1 depicts, in an exploded view, a needleless injection device according to the invention.

An injection device 1 according to the invention, as depicted in FIG. 1, has no needle and comprises a body (not shown) inserted under a cap 9 for actuating the device 1, this cap being closed off by a stopper 10. The device 1 will, for example, have a compact form, the advantages of which are more particularly described in patent No. FR 2 815 544. Actuation of such a device 1 by the patient, using the cap 9, is also described in patent FR 2 815 544. During the process of assembling the device 1, the body is intended to receive a plurality of elements. Thus, once assembled, the body comprises or delimits successively, from upstream to downstream, an initiator device, for example a percussion device, a primer, and a pyrotechnic charge, these three elements forming a gas generator, a combustion chamber, a reservoir 5 containing a liquid active substance to be injected, and an injection system.

According to the invention, the needleless injection device 1 comprises two main assemblies, namely a mechanical assembly and a pharmaceutical assembly 2. These two assemblies are distinct because, in general, they are produced separately, the construction of the pharmaceutical assembly 2 requiring specific monitoring and very close attention in particular as regards the filling with the active substance 53.

The mechanical assembly comprises in particular the gas generator and the mechanism for actuating the device according to the invention. The pharmaceutical assembly 2 comprises the container 5 for active substance 53 and the system for injection of the active substance 53.

Figure 3:
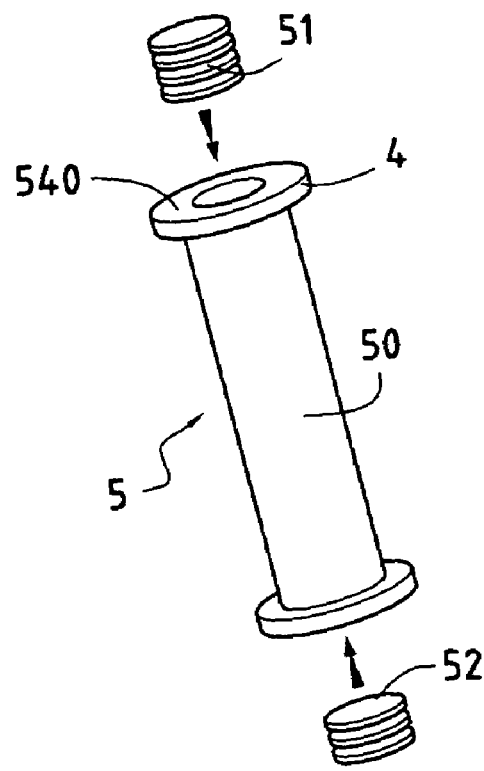
FIG. 3 depicts, in perspective, a container intended to receive the liquid active substance for injection.
Figure 6:
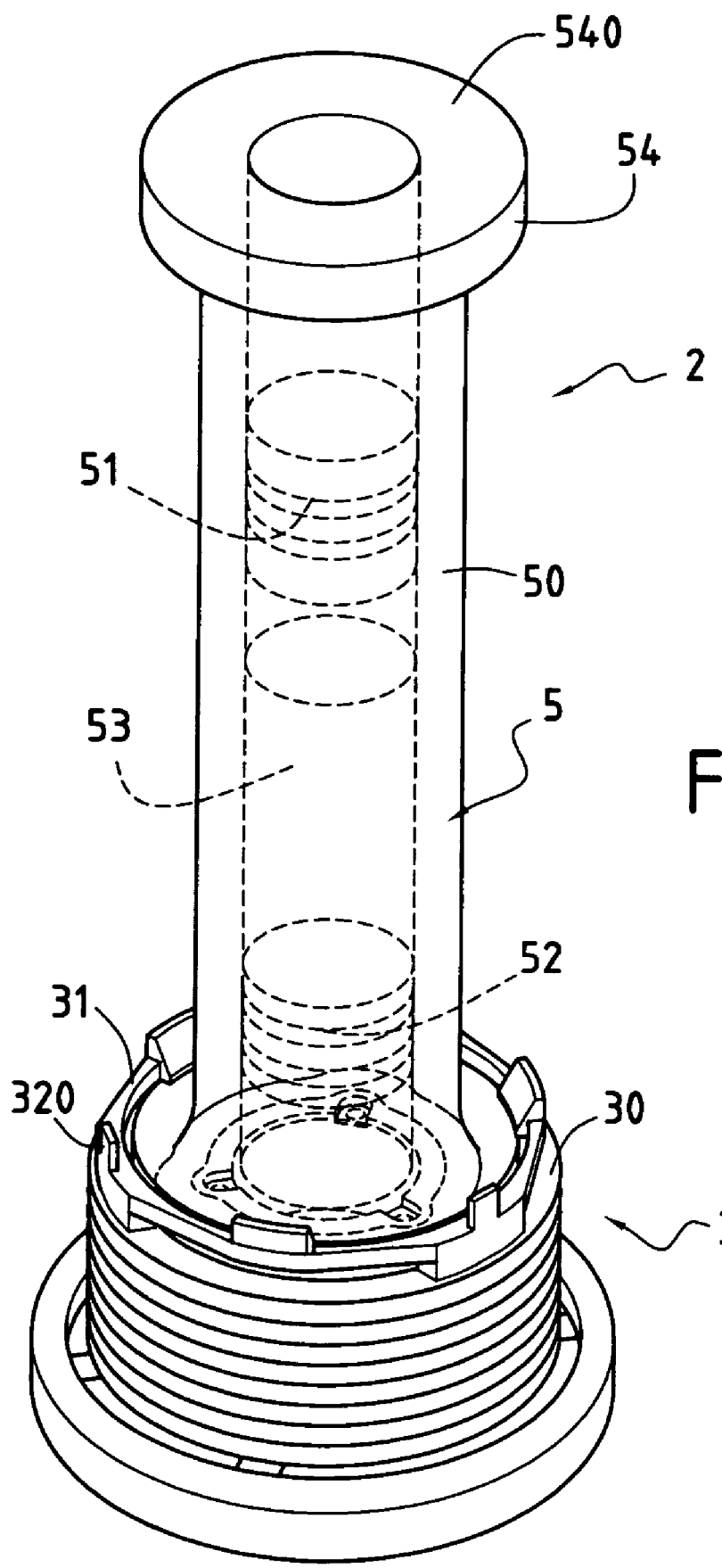
FIG. 6 depicts, in perspective, the container seen in FIG. 3, fitted on the injection nozzle to form a pharmaceutical assembly.
Figure 7:
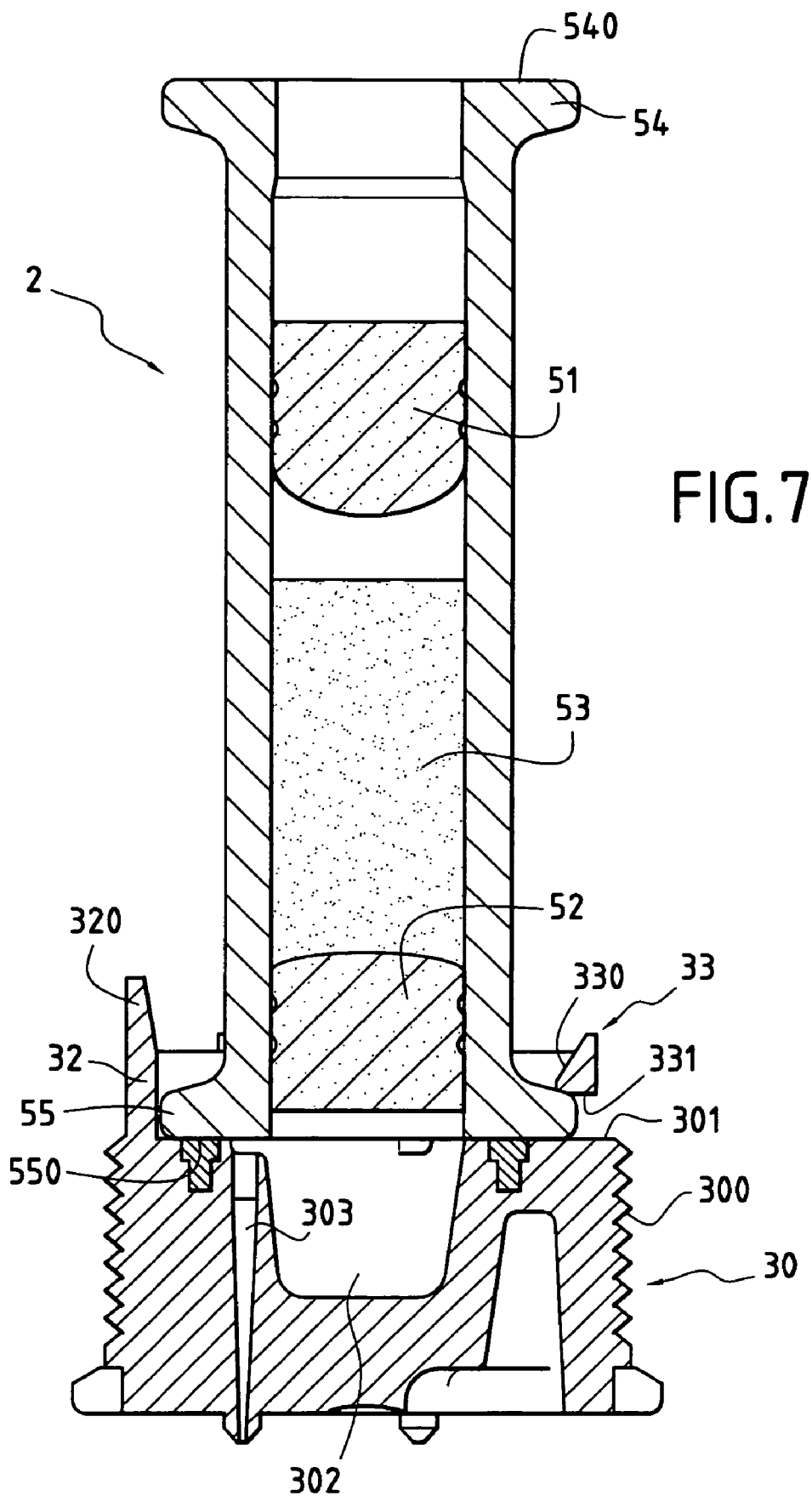
FIG. 7 depicts a cross section through the pharmaceutical assembly seen in FIG. 6.

The container 5 intended to receive the active substance 53 is shown in more detail in FIG. 3. It is formed, for example, by a glass tube 50 open at both ends. The tube 50 comprises a collar 54, 55 at each of its ends. At the end of the tube 50, each collar 54, 55 defines a flat annular surface 540, 550. The tube 50 is inserted into the body of the device 1 in such a way as to be connected, at its most upstream end, to the combustion chamber of the device 1, and, at its most downstream end, to the injection system. The active substance 53 (FIGS. 6 and 7) is, for example, held captive in the glass tube 50 between an upstream piston plug 51 and a downstream piston plug 52 which are inserted into the tube 50. The upstream 51 and downstream 52 piston plugs are made, for example, of an elastomer-based deformable material.

Figure 2:
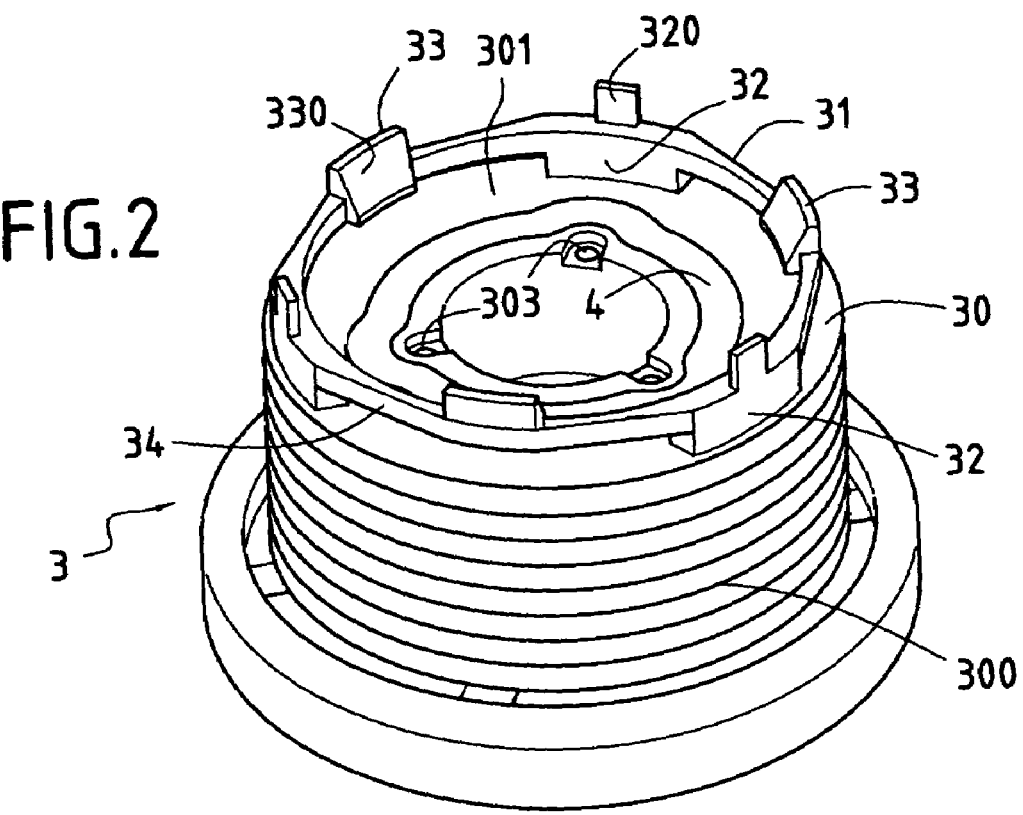
FIG. 2 depicts, in perspective, an injection nozzle used in the injection device according to the invention.

According to the invention, the injection system comprises an injection nozzle 3 through which the active substance 53 held in the container 5 is injected. The injection nozzle 3 comprises a cylindrical component 30 around which a thread 300 is formed so as to allow the nozzle 3 to be screwed onto the body of the needleless injection device 1. The cylindrical component 30 comprises a flat surface 301, forming a support plane for the tube 50, perpendicular to the axis A1 (FIG. 5) of the nozzle, at the center of which surface a blind hole 302 is formed. The cylindrical component 30 is traversed by a plurality of injection channels 303 along which the liquid flows at the time of injection. In FIG. 2, these channels 303 are three in number. They are formed parallel to the axis A1 of the nozzle 3, at the periphery of the blind hole 302 formed on the cylindrical component 30. At the end of the injection, the downstream piston plug 52 comes to sit in the blind hole 302, thus liberating the liquid active substance 53, which is then able to escape through the peripheral channels 303 communicating with the inside of the tube 50.

According to the invention, the nozzle 3 also comprises a crown 31 with a diameter substantially equal to the diameter of the cylindrical component 30. This crown 31 is in the form of a circular band arranged coaxially with respect to the axis A1 of the nozzle 3, the surface of said band being parallel to the axis A1 of the nozzle 3. This crown 31 is situated at a defined non-zero distance from the cylindrical component 30 and is connected to it by way of connecting blocks 32 on the surface of the cylindrical component 30 near the outer edge of the cylindrical component 30. These connecting blocks 32 are, for example, three in number and distributed in a balanced way between the crown 31 and the cylindrical component 30, that is to say at an angle of 60° relative to one another. Emerging from each block there is a rod 320, each rod 320 including, for example, an inclined part (FIG. 5) allowing the tube 50 to be guided when fitting it onto the nozzle 3. Arranged equidistantly between each block 32, that is to say offset 30° relative to each of the blocks 32, the crown 31 comprises a boss 33. Each boss 33 is elongate and inwardly curved following the curvature of the crown 31. The angle defined by the segments joining the center of the crown 31 to each of the two ends of a boss 33 is, for example, between 17° and 23° and is preferably 20°. Each boss 33 is formed by a portion 330 (FIG. 2) inclined with respect to the surface defined by the band. This portion 330 is inclined toward the inside of the nozzle 3 and in the direction of the cylindrical component 30 and is terminated by a flange 331. The summit or end of each of the bosses 33, defined as the connecting surface between the inclined portion 330 and the flange 331, has a rounded shape 332 (FIG. 5), with a radius equal to 0.1 mm, for example. The crown 31 has, for example, a diameter of 15 mm. The diameter of the crown 31 at the top of the boss 33 is, for example, 13.2 mm. The height of the band defining the crown is, for example, 1.4 mm. The thickness of the crown 31 is greater in the area of the blocks 32.

According to the invention, the tube 50 is intended to be fitted, at one of its ends, onto the nozzle 3 in order to form the pharmaceutical assembly 2. To do this, one of the ends of the tube 50 is clipped onto the nozzle 3. The space defined between the crown 31 and the cylindrical component 30 is substantially equal to the thickness of the collar 55 formed at one end of the tube 50. This space is thus sufficient to accommodate said collar 55. The tube 50 is inserted onto the nozzle 3 in such a way that its axis substantially coincides with the axis (A1) of the nozzle 3.

When fitting the tube 50 on the nozzle 3, the tube 50 is first guided by the rods 320 continuing the connecting blocks 32. The collar 55 situated at the end of the tube 50 then follows the inclined portions 330 of the bosses 33. The degree of inclination of the inclined portions 330 of the bosses 33 has an impact on the force that has to be expended to spread apart the bosses 33 and allow the collar 55 to pass. On continuing with fitting the tube 50, the collar 55 passes the summits of the bosses 33 and comes to sit under the bosses 33. The annular surface 550 situated at the end of the tube 50 is then held flat against the surface of the cylindrical component by way of the bosses 33. Each of the flanges 331 of the bosses 33 constitutes an anti-return element against the movement of extraction of the tube 50 relative to the nozzle 3.

According to the invention, the connecting branches 34 (FIG. 4) defined by the parts of the crown 31 supporting the bosses and joining the connecting blocks 32 are of a defined thickness and stiffness sufficient to guarantee the crown 31 a certain flexibility and thus to sufficiently spread apart the bosses 33 in order to allow the collar 55 of the tube 50 to pass when clipping the tube 50 onto the nozzle 3. Moreover, the connecting branches 34 must have a thickness and height sufficient to be sufficiently flexible and elastic and ensure that the bosses 33 match the shape of the glass tube 50.

According to the invention, the nozzle 3 will be made as one piece, for example. The material used for producing the nozzle 3 will have to be of a stiffness sufficient to guarantee that the tube 50 is held flat against the nozzle 3. Moreover, this material must not be aggressive with respect to glass and must be able to be used in pharmacy. Polycarbonate is a material satisfying these different criteria.

The space separating the crown 31 from the cylindrical component 30, in which space the collar 55 is inserted, must be chosen in such a way as to guarantee that the annular surface 550, defined at the end of the tube 50, is held flat against the surface 301 of the cylindrical component 30 and thereby guarantee a leaktight connection between the tube 50 and the nozzle 3.

According to the invention, when the pharmaceutical assembly 2 is fitted on the mechanical assembly to form the complete injection device 1, the leaktight connection between the tube 50 and the nozzle 3 is effected by the compression of a seal 4 (FIGS. 2 and 4) integrated in the nozzle 3.

The functioning of such a needleless injection device 1 having components such as those defined in this application is described in detail in French patent application FR 2 815 544. The overall functioning of such a device 1 may, however, be summarized as follows:

At rest, a striker of the percussion device bears, for example, against a stop with the aid of a pretensioned spring whose axis is more or less coincident with the axis of the striker. A maneuver on the part of the patient releases the striker which, under the effect of the relaxation of the spring, will strike the primer situated on the same axis. Initiation of the primer then leads to ignition of the pyrotechnic charge of the gas generator. Under the action of the gases generated by the pyrotechnic charge, the upstream piston plug 51 present in the tube 50 of the container 5 is displaced and in turn pushes the active substance 53 in the direction of the injection system. The downstream piston plug 52 is itself pushed until it comes to sit in the blind hole 302 of the injection nozzle 3. Thus, the communication between the inside of the tube and the peripheral channels is formed and, as a result, the active substance 53 can reach the peripheral channels 303 and be ejected out of the device 1.

It will be obvious to those skilled in the art that the present invention allows embodiments in numerous other specific forms without departing from the scope of application of the invention as claimed. Consequently, the present embodiments are to be considered by way of illustration and may be modified within the scope defined by the attached claims, nor need the invention be limited to the details given hereinabove.

The invention claimed is:

1. An injection device comprising
   an injection nozzle and a reservoir intended to hold captive an active substance that is to be injected through the injection nozzle,
   an upstream piston plug and a downstream piston plug fitted within the reservoir,
   said injection nozzle comprising a flat surface forming a support plane for said reservoir,
   a blind hole formed proximate a center of said flat surface, said blind hole sized to receive said downstream piston plug upon injection,
   two or more peripheral channels defined within said injection nozzle proximate a periphery of the blind hole, said peripheral channels configured to deliver the active substance upon injection,
   said reservoir being fixed to said nozzle with the aid of connecting means, said reservoir including a collar which is situated at one of the ends of said reservoir, said collar extending in an outwardly direction from a surface of said reservoir,
   the connecting means comprising at least three bosses which are integral with the nozzle, each of said bosses being arranged on one plane that extends parallel to said collar in said outwardly direction, each of said bosses comprising an inclined part that is inclined with respect to the one plane, each inclined part being terminated by a flange, said flange cooperating with said collar, said collar serving as an anti-return element for the reservoir when the latter is connected to the nozzle, and said device being characterized in that the bosses are connected to one another by connecting branches.

2. The device as claimed in claim 1, characterized in that the inclined part of the bosses is inclined in the direction of the nozzle and toward the inside of the nozzle.

3. The device as claimed in claim 1, characterized in that each boss is inwardly curved, the bosses being inscribed in a same circle whose diameter is substantially equal to an external diameter of the collar of the reservoir.

4. The device as claimed in claim 3, characterized in that an angle of opening defined by two segments joining the center of the circle to the ends of each inwardly curved boss is between 17 and 23 degrees.

5. The device as claimed in claim 1, characterized in that the bosses are spaced apart from one another at regular intervals.

6. The device as claimed in claim 1, characterized in that the nozzle has a flat surface, the bosses being situated at a non-zero distance from said surface, the space between the flange of the bosses and said surface substantially corresponding to the thickness of the collar of the reservoir.

7. The device as claimed in claim 1, characterized in that the end of each of the bosses has a rounded shape.

8. The device as claimed in claim 7, characterized in that the diameter of the circle is 13.2 mm, and in that the rounded shape has a radius of 0.1 mm.

9. The device as claimed in claim 1, characterized in that each boss is supported by a rod which is fixed to the nozzle and is able to deform elastically.

10. The device as claimed in claim 1, characterized in that the connecting branches have a height of 1.4 mm.

11. The device as claimed in claim 1, characterized in that the bosses are supported by the connecting branches, said connecting branches being made integral with the nozzle by means of connecting blocks and being connected to one another so as to define a substantially circular crown whose diameter is substantially equal to the external diameter of the collar of the reservoir.

12. The device as claimed in claim 11, characterized in that the nozzle, the bosses, the connecting branches and the connecting blocks are made as one piece.

13. The device as claimed in claim 12, characterized in that the piece is made from polycarbonate.

14. The device as claimed in claim 1, characterized in that the collar defines a flat annular surface circumscribing said one of the ends of said reservoir.

\* \* \* \* \*